(12) United States Patent
Jaisson (10) Patent No.: US 12,171,625 B2
(45) Date of Patent: Dec. 24, 2024

(54) METHOD FOR ANIMATING MODELS OF THE MANDIBULAR AND MAXILLARY ARCHES OF A PATIENT IN A CORRECTED INTERMAXILLARY RELATIONSHIP

(71) Applicant: MODJAW, Ste Helene du Lac (FR)

(72) Inventor: Maxime Jaisson, Les Marches (FR)

(73) Assignee: MODJAW, Villeurbanne (FR)

( * ) Notice: Subject to any disclaimer, the term of this patent is extended or adjusted under 35 U.S.C. 154(b) by 456 days.

(21) Appl. No.: 17/293,180

(22) PCT Filed: Nov. 25, 2019

(86) PCT No.: PCT/FR2019/052798
§ 371 (c)(1),
(2) Date: May 12, 2021

(87) PCT Pub. No.: WO2020/104760
PCT Pub. Date: May 28, 2020

(65) Prior Publication Data
US 2022/0008174 A1    Jan. 13, 2022

(30) Foreign Application Priority Data

Nov. 23, 2018 (FR) ...................................... 1871744

(51) Int. Cl.
*A61C 11/00* (2006.01)
*A61C 7/00* (2006.01)
(Continued)

(52) U.S. Cl.
CPC ............ *A61C 11/006* (2013.01); *A61C 7/002* (2013.01); *A61C 11/02* (2013.01); *A61C 11/06* (2013.01);
(Continued)

(58) Field of Classification Search
None
See application file for complete search history.

(56) References Cited

U.S. PATENT DOCUMENTS

2002/0048741 A1    4/2002    Jordan et al.
2005/0107687 A1    5/2005    Anderson
(Continued)

FOREIGN PATENT DOCUMENTS

CN          1833617 A       9/2006
WO      WO2013/030511 A1    4/2016
WO      WO2016/062962 A1    4/2016

OTHER PUBLICATIONS

Preliminary Search in co-pending related French Application No. FR 1871744, mailed Sep. 27, 2019.
(Continued)

*Primary Examiner* — Sultana M Zalalee
(74) *Attorney, Agent, or Firm* — Thomas | Horstemeyer, LLP (57) ABSTRACT

The invention relates to a method for animating models of the mandibular and maxillary arches of a patient in a corrected intermaxillary relationship, comprising: —providing three-dimensional numerical models (MD, MX) of the mandibular and maxillary arches of the patient; —providing a recording of the mandibular motion of the patient, said recording comprising a plurality of relative positions of the mandible of the patient with respect to the maxilla; —selecting, from said positions, a reference position (X) of the mandible with respect to the maxilla of the patient; —determining a target position (Y) for the mandible with respect to the maxilla, said target position defining a corrected intermaxillary relationship for the patient; —determining a rigid transformation between the reference position (X) and the target position (Y); —applying said rigid transformation (i) to the recording of the mandibular motion of the patient (Continued)

in order to animate the three-dimensional numerical models of the mandibular and maxillary arches, or (ii) to the three-dimensional numerical model of the mandible, the delivered recording of the mandibular motion being applied to the three-dimensional numerical models of the mandible and of the maxilla in order to animate said models.

15 Claims, 4 Drawing Sheets

(51) Int. Cl.
    *A61C 11/02*     (2006.01)
    *A61C 11/06*     (2006.01)
    *G06T 7/73*     (2017.01)
    *G16H 50/50*     (2018.01)

(52) U.S. Cl.
    CPC .............. *G06T 7/73* (2017.01); *G16H 50/50* (2018.01); *G06T 2207/30036* (2013.01)

(56) References Cited

U.S. PATENT DOCUMENTS

| | | |
|---|---|---|
| 2009/0068617 A1 | 3/2009 | Lauren |
| 2009/0082989 A1 | 3/2009 | Zuhars |
| 2011/0004430 A1 | 1/2011 | Nieminen |
| 2011/0045428 A1* | 2/2011 | Boltunov ................. G06T 7/70 433/24 |
| 2011/0191081 A1 | 8/2011 | Malfliet et al. |
| 2014/0294273 A1* | 10/2014 | Jaisson ............... A61B 5/0035 382/131 |
| 2016/0378883 A1* | 12/2016 | Lucas ...................... A61F 5/56 703/1 |
| 2017/0209072 A1 | 7/2017 | Oren |
| 2018/0005377 A1 | 1/2018 | Alvarez et al. |
| 2018/0049855 A1* | 2/2018 | Takahashi .......... A61C 13/0004 |
| 2018/0336736 A1* | 11/2018 | Kim ......................... G06T 7/60 |
| 2019/0000559 A1 | 1/2019 | Berman |
| 2019/0000592 A1* | 1/2019 | Cam ................... A63B 71/085 |
| 2020/0060796 A1* | 2/2020 | Clauss ................ A61C 19/045 |
| 2020/0268495 A1* | 8/2020 | Ryakhovsky .......... A61C 13/34 |
| 2020/0319267 A1 | 10/2020 | Ashe |

OTHER PUBLICATIONS

International Search Report in co-pending related, PCT Application No. PCT/FR2019/052798, mailed Jun. 16, 2020.

Jean-Francois Lasserre « Comprendre l'augmentation de DVO dans les approches minimales invasives des traitements de l'usure et des anomalies de l'email » Quintessence International, OA News, May 2016.

* cited by examiner

METHOD FOR ANIMATING MODELS OF THE MANDIBULAR AND MAXILLARY ARCHES OF A PATIENT IN A CORRECTED INTERMAXILLARY RELATIONSHIP

CROSS REFERENCE TO RELATED APPLICATIONS

This application is the 35 U.S.C. § 371 national stage application of PCT Application No. PCT/FR2019/052798, filed Nov. 25, 2019, which application claims the benefit of French Application No. FR 1871744, filed Nov. 23, 2018, both of which are hereby incorporated by reference herein in their entireties.

FIELD OF THE INVENTION

The present invention lies in the field of dentistry. More precisely, it relates to a method for animating models of the mandibular and maxillary arches of a patient in a corrected intermaxillary relationship.

STATE OF THE ART

The vertical dimension of occlusion (often referred to as VDO) is an important quantity of an individual's face, both aesthetically (harmony of proportions) and functionally (comfort associated with the temporomandibular function).

The vertical dimension of occlusion is generally defined as the height of the lower part of the face, or, more simply, the distance between the subnasale and the gnathion, during the occlusion phase. Conventionally, the subnasale is defined as the anterior nasal spine, while the gnathion is the most anterior point of the most sloping part of the chin protuberance.

In dentistry, it is sometimes necessary to increase the vertical dimension of occlusion of a patient. This increase may be due to the fact that the patient has lost his or her original vertical dimension of occlusion, for example due to chemical or mechanical erosion of the teeth. Another indication for an increase in the vertical dimension of occlusion can be the implementation of a therapeutic treatment that requires sufficient space for the placement of prostheses or orthodontic appliances.

Increasing the vertical dimension of occlusion requires changing the position of the mandible relative to the maxilla (also known as the intermaxillary relationship (IMR)), which yields a change in the zone where the dental arches meet. Depending on the extent of the increase, the mandible can be moved only in a vertical direction and possibly in an antero-posterior direction.

Figure 1A:
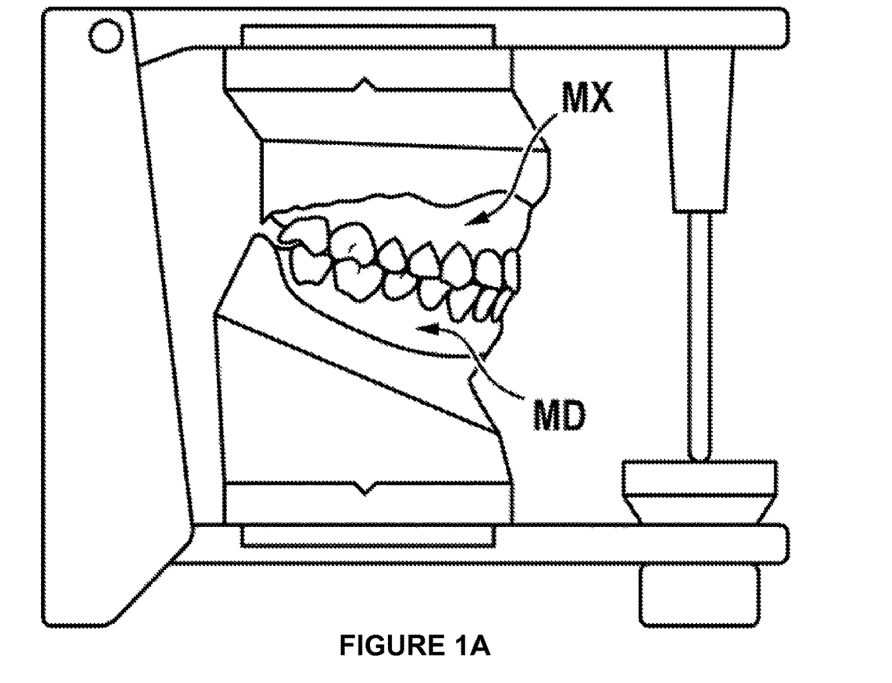
FIG. 1A illustrates a physiological articulator before increasing the vertical dimension of occlusion.
Figure 1B:
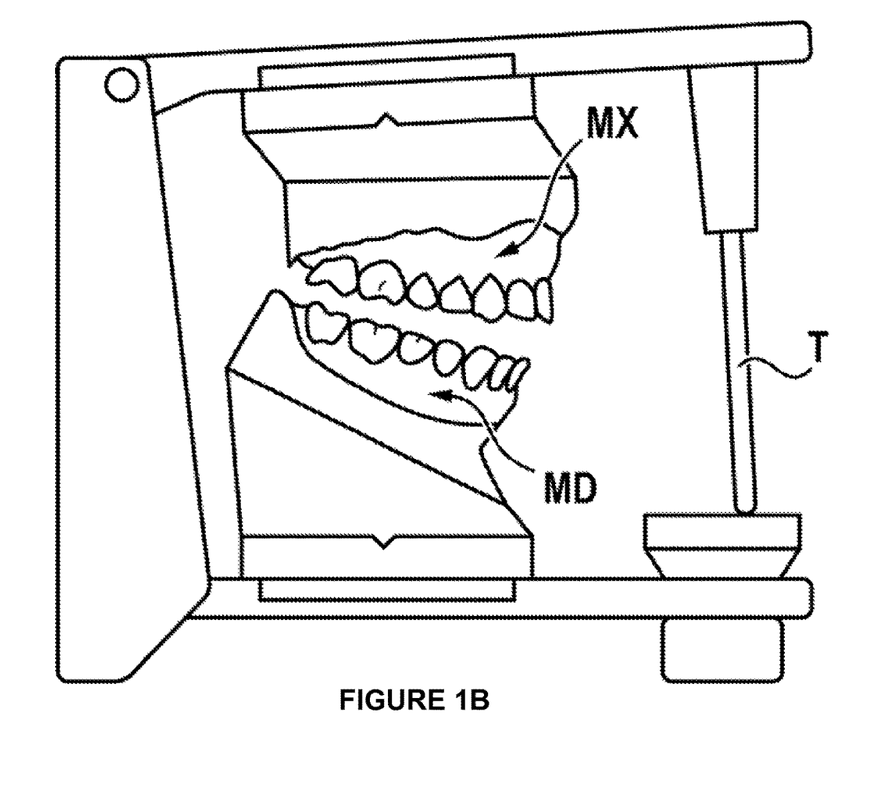
FIG. 1B illustrates the physiological articulator of FIG. 1A after increasing the vertical dimension of occlusion.

To make sure that this new intermaxillary relationship will be comfortable and relevant for the patient, the practitioner has to simulate motions applied to the dental arches, using a mechanical or virtual articulator using three-dimensional physical or digital models of the mandibular arch and maxillary arch. The choice of the new mandibular position is performed by recording in the mouth on a wax sheet or by injecting a chemically setting material. When the mandibular movement is only vertical, the change can be made directly on the articulator, by moving the incisal rod T so that the model of the mandibular arch MD is spaced from the model of the maxillary arch MX by a distance equal to the desired increase in the vertical dimension of occlusion (see FIGS. 1A and 1B). However, it is recommended that a facebow be used in order to locate the models relative to the axis of rotation of the mandible so that the arch spacing is as close to reality as possible.

However, such articulators provide inaccurate simulations as the applied kinematics is approximated and does not correspond to the patient's real mandibular kinematics (also called real function).

DISCLOSURE OF THE INVENTION

One aim of the invention is to overcome drawbacks of known techniques and to provide a method for animating models of the mandibular and maxillary arches of a patient in a corrected intermaxillary relationship.

To this end, the invention provides a method for animating models of the mandibular and maxillary arches of a patient in a corrected intermaxillary relationship, comprising:

providing three-dimensional digital models of the patient's mandibular and maxillary arches, providing a record of the patient's mandibular kinematics, said record comprising a plurality of relative positions of the patient's mandible with respect to the maxilla, selecting, from said positions, a reference position of the mandible relative to the patient's maxilla, determining a target position of the mandible relative to the maxilla, said target position defining a corrected intermaxillary relationship of the patient, determining a rigid transformation between the reference position (X) and the target position, applying said rigid transformation to (i) the record of the patient's mandibular kinematics to animate the three-dimensional digital models of the mandibular and maxillary arches with the record resulting from the application of said rigid transformation, or (ii) the three-dimensional digital model of the mandible, the record of the mandibular kinematics provided being applied to the three-dimensional digital models of the mandible and maxilla resulting from the application of said rigid transformation to animate said models.

As the reference position is present in the record of the mandibular kinematics, the mandibular kinematics data is attached to this reference position. The present invention allows said data to be transposed to another so-called target position.

According to one embodiment, the reference position is the patient's reference occlusal position before correcting the intermaxillary relationship.

According to one embodiment, the record of the patient's mandibular kinematics describes the trajectory of markers integral with the mandible, and the rigid transformation is a transformation for switching from the position of the markers in the reference position to the position of the markers in the target position.

The target position may be chosen by the user from the set of relative positions of the mandible relative to the maxilla in the record of the mandibular kinematics.

Alternatively, the method comprises automatically preselecting a set of relative positions of the mandible relative to the maxilla, said set of positions being chosen such that each position of said set defines a vertical dimension of occlusion within a determined range.

Advantageously, said preselection may be made from previously provided clinical criteria.

In other embodiments, the target position is not part of the set of positions present in the record of the mandibular kinematics, but may be simulated. To this end, the method advantageously comprises determining an axis of rotation of the mandible and creating virtual positions of the mandible along the path of rotation towards increasing or decreasing the vertical dimension of occlusion, the target position being chosen from said virtual positions.

In some embodiments, the target position is chosen such that the vertical dimension of occlusion (VDO) is increased by a value less than a threshold chosen so as not to cause a displacement of the axis of rotation of the mandibular condyles relative to the patient's temporal fossa.

Preferably, the target position is chosen such that the vertical dimension of occlusion defined at the incisor crown end is increased by less than 20 mm relative to the vertical dimension of occlusion defined by the patient's reference occlusal position.

In other embodiments, the target position is chosen so that the vertical dimension of occlusion (VDO) is decreased.

In animating the models of the mandibular and maxillary arches, the reference occlusal position of the mandible relative to the maxilla in the corrected intermaxillary relationship becomes the target position.

BRIEF DESCRIPTION OF THE FIGURES

Further characteristics and advantages of the invention will become apparent from the following detailed description, with reference to the appended drawings in which.

DETAILED DESCRIPTION OF EMBODIMENTS OF THE INVENTION

The method described below is computer-implemented. The system for implementing the method comprises:
a computer comprising a processor for receiving data previously obtained, especially digital models of the patient's mandibular and maxillary arches and a record of the patient's mandibular kinematics, and for running animation and modelling algorithms, and
a screen for displaying the various steps implemented during the method, with a user interface allowing the practitioner to input treatment parameters and to view the mandibular kinematics before and after correction.

Obtaining Three-Dimensional Digital Models of the Mandibular and Maxillary Arches Prior to the implementation of the method, the dental arches were scanned in a known and reproducible meshing relationship. A tool that can be used for this purpose is an intraoral optical impression camera. Such a camera is used to scan one arch and then the other, as well as a vestibular (sideways) impression of the meshing teeth to know the position of one arch relative to the other. This operation is known per se and is not as such part of the invention.

Another method can consist in using a tabletop scanner. This scans plaster models from physicochemical impressions one after the other and then in the meshing position.

Other methods are also contemplatable, such as radiographic cone beam scanning of a plaster model or a silicone impression of the dental arches.

The invention can indeed be implemented with any three-dimensional digital model of dental arches generated by commercially available digitizing techniques. The result of these digitizing operations is a surface grid of the maxillary arch and mandibular arch. Each grid is defined in an orthonormal reference frame of the digitizing device.

Recording the Mandibular Kinematics

The purpose of recording the mandibular kinematics is to provide information on how the mandible moves in space, and to use this kinematics to animate the three-dimensional models of the dental arches with a view to guiding the design of a dental prosthesis or other corrective device (orthodontic appliance, splint, . . . )

One embodiment of this recording, as well as of the reset of the models of the dental arches relative to reference planes or axes of the patient has already been described in document WO 2013/030511 and can be implemented in the present invention, however the invention being not limited to the techniques described in that document.

Generally speaking, recording the mandibular kinematics is implemented by equipping the patient with at least one marker integral with the patient's forehead (or any other location on the face integral with the maxilla) and at least one marker integral with the mandibular arch (by attachment to the mandible via a support or by direct attachment to the teeth), and by locating and recording the movements of said markers by means of a camera during mandibular motions of the patient.

Depending on the camera technology, the markers can be diodes, black and white or coloured test patterns, or spheres, lands or other reflective objects. The movement of the markers in the mandible is tracked by the camera relative to the markers in the forehead. A rigid transformation enables the motion of the model of the mandibular arch relative to the model of the maxillary arch to be derived.

It is possible to dispense with a frontal marker by implementing a facial recognition technique as described in document WO 2016/062962. This technique indeed allows the determination, from stereoscopic images, of reference points and planes of the patient, in relationship to which the movement of the mandibular markers is tracked.

The invention is not limited to any particular technique for acquiring mandibular kinematics. For example, the movement of the mandible relative to the maxilla can be recorded by means of accelerometers or inertial units integral with the jaws.

Determining the Reference Position and Target Position

The record of the mandibular kinematics comprises a plurality of successive positions of the mandible relative to the maxilla during motions performed by the patient (for example mastication).

The record is in the form of a digital file comprising a plurality of frames each corresponding to a relative position of the mandible and the maxilla.

In particular, this digital file comprises a frame corresponding to a reference position of the patient (for example, but not limited to, the reference occlusal position). It is to this reference position that the mandibular kinematics data is attached.

In some embodiments, this digital file can further comprise a frame corresponding to a target position intended to become the patient's new reference position after implementing the correction.

In other embodiments, especially if none of the frames of the record of the mandibular kinematics correspond to a suitable target position for the practitioner, the practitioner can simulate the target position. For this purpose, using the record of the mandibular kinematics, an algorithm can determine the joint axis of the mandible relative to the maxilla. This axis typically passes through the condyles. The practitioner can then simulate a rotation of the digital model of the mandibular arch about this axis to determine a preferred position of the mandible relative to the maxilla. This preferred position is chosen as the target position. One or more frames can be created to represent virtual positions of the mandible along the path of rotation towards opening or decreasing the vertical dimension of occlusion. In practice, these additional frames are created by applying a rigid rotation-only transformation about the previously determined axis of rotation of the condyles, to the three-dimensional models of the frames recorded. These additional frames are added to the frames of the actually recorded mandibular kinematics. The target position can then be a second frame chosen by the practitioner from the additional frame(s).

Figure 2A:
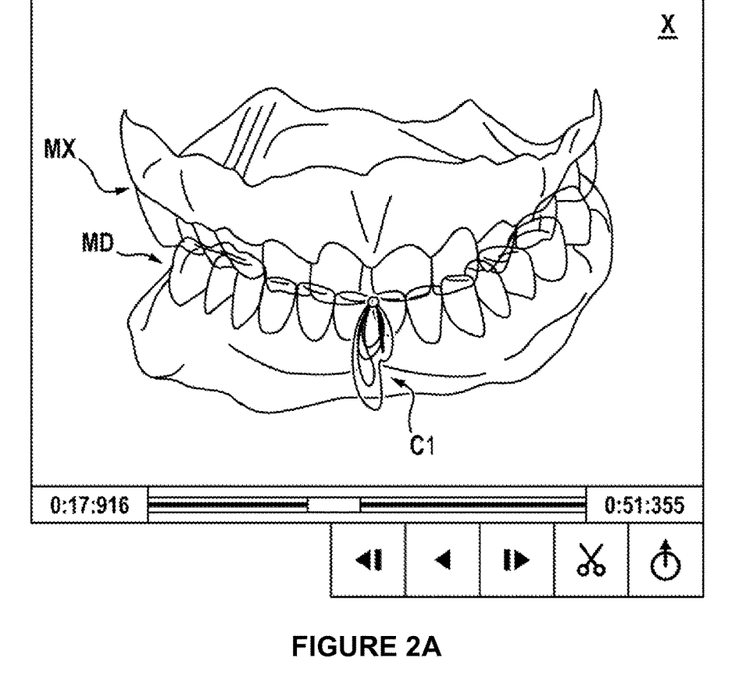
FIG. 2A illustrates the record of the patient's mandibular kinematics before correcting the intermaxillary relationship.
Figure 2B:
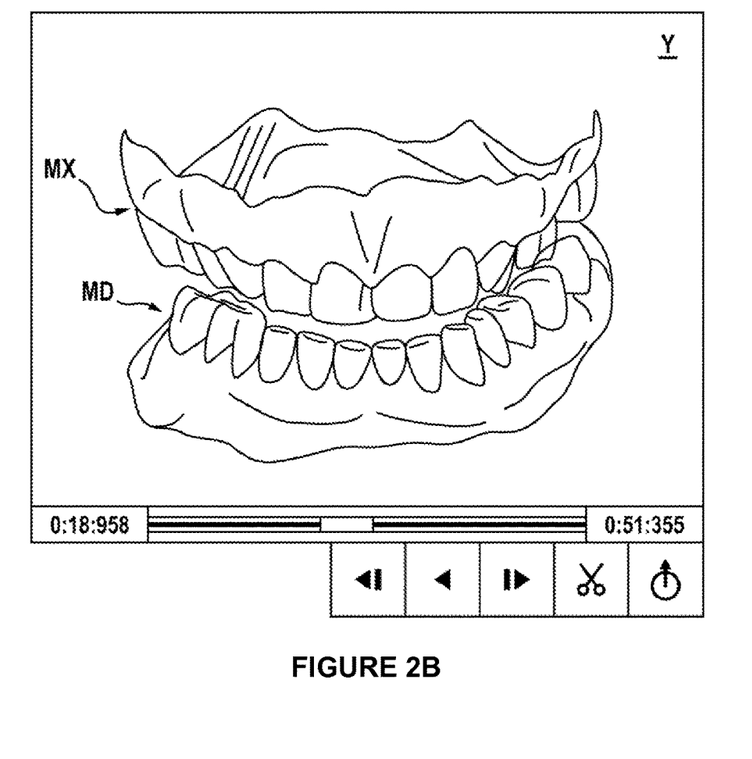
FIG. 2B illustrates the choice of the frame defining the target position of the mandible in the corrected intermaxillary relationship.
Figure 2C:
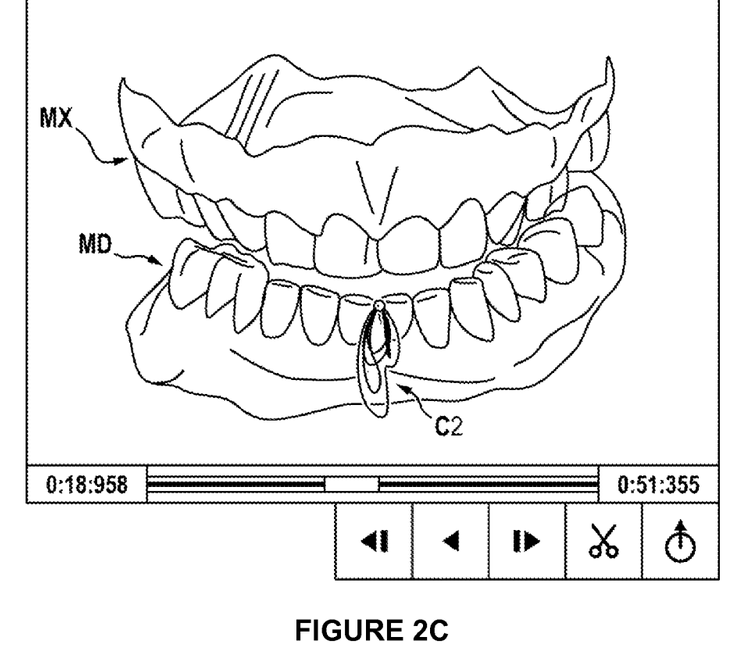
FIG. 2C illustrates the application of the record of the patient's mandibular kinematics after correcting the intermaxillary relationship.

FIGS. 2A to 2C illustrate the record of the patient's mandibular kinematics before (FIG. 2A) and after (FIG. 2C) correcting the intermaxillary relationship respectively.

The user can display this record on the screen and play it as many times as necessary. For this purpose, he/she has a user interface provided with a display zone to view the motions of the mandibular arch MD and maxillary arch MX and buttons for switching from one frame to the other and for exporting a particular frame.

The user selects a first frame X that corresponds to the patient's reference position.

According to one embodiment, the reference position is conventionally that of the first frame of the record of the mandibular kinematics. In general, the patient is supposed to start the recording with the teeth clenched, which corresponds to the meshing position of the digital models of the arches, so-called a reference occlusal position.

According to another embodiment, the practitioner can be required to place an interocclusal device (for example a splint) upon recording the mandibular kinematics to guide mandibular motions and find a particular position of the mandible relative to the maxilla, other than the initial meshing position.

The person skilled in the art can possibly define other criteria to define the reference position.

FIG. 2A illustrates, for example, the mandibular arch MD in said reference position. The mandibular kinematics is represented as curve C1 which illustrates the patient's mastication pattern at the incisor crown end.

The user additionally selects a second frame Y which corresponds to the target position intended to become the patient's new reference position (see FIG. 2B). This target position is associated with a corrected intermaxillary relationship, for example corresponding to a vertical dimension of occlusion increased or decreased relative to the patient's initial vertical dimension of occlusion.

The user can select the second frame Y from all the frames making up the record. This is done using the user's technical expertise to determine the amplitude of increase or decrease in the vertical dimension of occlusion adapted for the patient. This selection is made on the opening-closing path by choosing a repeatable motion. This motion can be generated by the patient himself/herself or guided by the practitioner who manipulates the patient's mandible to feel the terminal axial motion and verify that the return to occlusion is always at the same inter-arch meeting point.

Alternatively, an algorithm for processing the record of the mandibular kinematics can preselect a set of frames, so as to limit the user's choice to a limited number of frames each corresponding to a vertical dimension of occlusion within a determined range. "Artificial intelligence" type algorithms can be used for this purpose. This preselection is advantageously based on clinical criteria previously input into the algorithm.

For example, the article by Jean-François Lasserre [1] can be referred to, which provides rules to be observed when increasing the vertical dimension of occlusion. One of these rules is called the "⅓ rule"; it takes account of the fact that, on a physiological articulator, for the same increase in VDO of the lower face, the opening between the incisal rod and the incisal table is three times the opening between the second molars, and the opening between the central incisors is twice that between the second molars. Another rule is the so-called "functional voids" or "1+1=3" rule, reflects the fact that when making antagonistic overlays, functional occlusal voids, which are about 1 mm thick for overlays each 1 mm thick, have to be taken into account in addition to the thickness of said overlays.

Based on these rules, the software can provide, when the practitioner seeks to determine a new mandibular position, a situation of the mandible such that the first molars are spaced 3 mm apart, which is the minimum space for making resistant prostheses. On the rotation path, the software thereby stops the mandible once this space is reached.

Alternatively, cephalometric tracings on a profile radiograph can be used to determine the target position of the mandible in a sagittal plane by virtue of the calculation of certain angles. The profile radiograph imported into the software is superimposed on the 3D models. The results of the cephalometric analysis suggest a position of the mandible in the path of the prerecorded motions.

According to another embodiment, the deglutition motion allows, in certain clinical situations, the vertical dimension of occlusion to be chosen, especially for an edentulous patient. Indeed, the mandible pauses on a highest position, which is a position that the software can suggest to the practitioner.

As indicated above, the target position may not be chosen as a frame of the record of the mandibular kinematics, but can be simulated.

Figure 3:
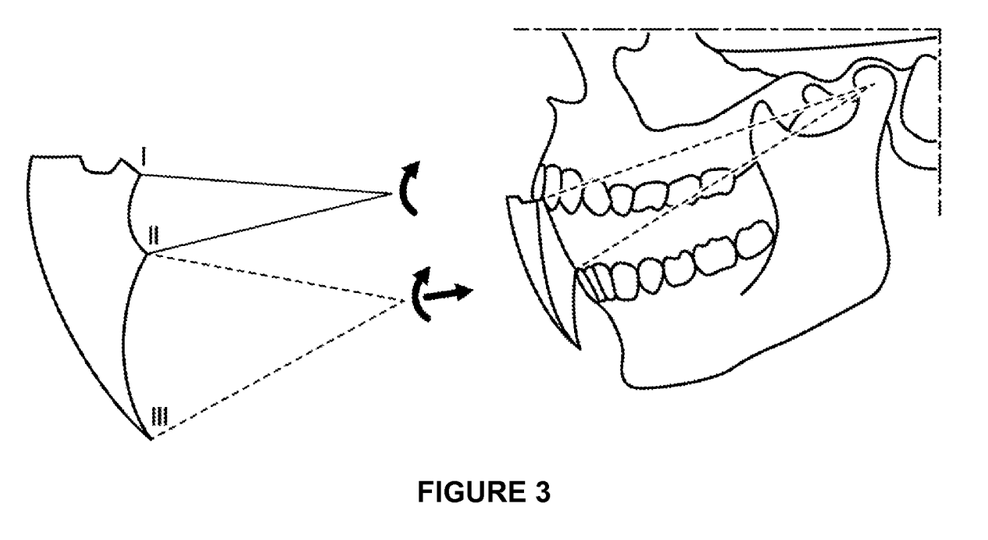
FIG. 3 schematically sets forth movements of the mandible as a function of the opening caused by the increase in the vertical dimension of occlusion.

In general, it is preferable to limit the increase in the vertical dimension of occlusion below some threshold. Indeed, the mandibular motion is guided by the patient's teeth, temporomandibular joint and neuromuscular activity. As illustrated in FIG. 3, as long as the increase in the vertical dimension of occlusion is less than said threshold (opening from I to II), the axis of rotation of the condyles remains in the temporal fossa and the muscles of the joint remain in their resilient range; in this case, only changes in the dentition are likely to alter mandibular motion. On the other hand, if the increase in the vertical dimension of occlusion is greater than the threshold (II to III opening), a translation of the mandible in a horizontal plane, a suppression of dental guidance and a modification of muscle activity also occur; in this case, the envelope of the mandibular motion is modified, which is desired to be avoided.

In practice, the target position is preferably chosen so that the vertical dimension of occlusion defined at the incisor crown end is increased by less than 20 mm relative to the vertical dimension of occlusion defined by the patient's initial reference occlusal position, so as not to move the axis of rotation of the condyles.

In some cases, the practitioner may rather be confronted with the need to decrease the patient's vertical dimension of occlusion. This is the case, for example, when correcting prematurity, that is, contacts which, for pathological reasons, occur prematurely during rotation of the mandible. A prematurity can, for example, be caused by a tooth that is too prominent relative to the arch to which it belongs. However, the mandibular kinematics can be correct. The target position can be determined by simulating an abrasion of the prominent tooth and simulating the resulting jaw closure.

Another example relates to a case where the patient is equipped with a splint that prevents or at least reduces erratic motions of the mandible as part of a neuromuscular reconditioning treatment; such a splint creates an extra thickness in the arch that it covers and is likely to increase the vertical distance of occlusion relative to the post-treatment situation where the patient is not wearing the splint. In this case, the mandibular kinematics generated by wearing the splint is of interest to the practitioner.

There are different ways of proceeding in the case of the use of a splint.

According to one embodiment, the dental arches are scanned with the splint in place on the mandible or maxilla, and in the occlusal position on the splint. The reference position (marked by the first X-frame) corresponds to this situation. The target position can exist in the record of the mandibular kinematics or can be simulated. The target position can exist if the record of the mandibular kinematics starts with the splint in place and then the practitioner removes the splint from the patient's mouth upon recording, and the patient moves to or is guided to the target position, shown as a second frame Y. The target position can be simulated by being chosen along the simulated path of the mandible during rotation about its axis.

According to another embodiment, the dental arches are scanned without the splint and in the dental meshing position. At start of the recording of the mandibular kinematics, the first frame is the position of the arches in occlusion, as scanned, and then, during this same recording, the splint is placed on one of the two arches and mandibular movement exercises are performed. The reference position corresponds to the frame at the moment the splint is in place (the kinematics to be transposed being the one when the patient is in contact with the splint). The practitioner computationally validates it as such and also selects the part of the mandibular kinematics attached to this new reference position that he/she will transpose to the target position. On the screen, the two models of dental arches are seen moving with a space between them. Then the target position is chosen as a frame from the recording or simulated. If the target position is chosen, it can be the first frame of the recording or another position corresponding to another frame of the part of the record in which the splint is not in place. The simulation of the target position has been described above.

Determining the Rigid Transformation

Once the frames X and Y have been chosen, an algorithm calculates a rigid transformation from the frame X to the frame Y.

Different methods can be used to calculate this rigid transformation. According to a preferred embodiment, this calculation is based on the trajectories of the markers integral with the mandible and maxilla upon recording the mandibular kinematics. The rigid transformation is the transformation for switching from the position of the markers in frame X to the position of said markers in frame Y. For example, if the position of MD relative to MX in frame X (respectively frame Y) is represented by the matrix Tx (respectively Ty), then the rigid transformation of MD from frame X to frame Y is represented by the matrix $(Ty)^{-1} * Tx$.

Of course, the person skilled in the art could use other methods for calculating the rigid transformation depending on the record available.

Animating the Arch Models

With reference to FIG. 2C, an algorithm applies the previously calculated rigid transformation (curve C2) to the recorded mandibular kinematics. The models of the mandibular and maxillary arches are then animated with the kinematics C2.

Alternatively, an algorithm applies the rigid transformation to the model of the mandibular arch and animates the models of arches that have undergone said rigid transformation with the patient's initially recorded mandibular kinematics.

The person skilled in the art can choose either of these animation methods according to the possible computing and mathematical constraints they are confronted with to implement the method.

Figure 4:
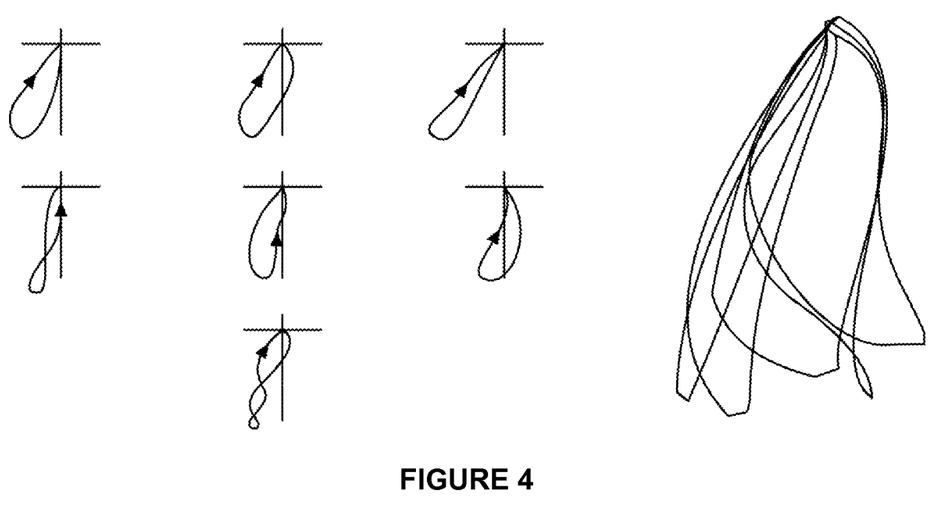
FIG. 4 illustrates different mastication patterns recorded at the incisor crown end for functional and dysfunctional cycles.

Advantageously, the practitioner checks whether the patient's mandibular kinematics is functional or dysfunctional before implementing the rest of the method and especially before transposing this kinematics to the corrected intermaxillary relationship. To this end, he/she can trace a mastication pattern and compare this pattern with types of patterns identified as functional or dysfunctional. FIG. 4 illustrates, on the left hand side, theoretical mastication patterns at the incisor crown end for functional cycles (the top three cycles) and dysfunctional cycles (the bottom four cycles). The right-hand side of FIG. 4 illustrates a clinical pattern, which is considered as functional. Of course, the person skilled in the art could trace a mastication pattern recorded at a point other than the incisor crown end, for example the condyles. The method described above is only implemented if the patient's mandibular kinematics is functional. In the case where the patient's mandibular kinematics is dysfunctional, the practitioner will turn to other tools, such as an articulator.

Applications

The method just described can find application in orthodontics, placement of dental prostheses or maxillofacial surgery.

For example, there are situations where a patient's teeth can be abraded by mechanical stress (bruxism) or by chemical erosion due to the consumption of acidic foods or drinks. The teeth can be natural or prosthetic. This tooth destruction occurs slowly and the masticatory function has time to sculpt the teeth by keeping the essential guides on the occlusal tables, despite their destruction and loss of vertical dimension. To treat such a patient, a complementary examination of the health of the manducatory apparatus (muscles and joints) is established prior to the implementation of the present invention. If the result is positive, the practitioner will be willing to preserve the way the mandible moves, but will have to restore the vertical dimension of occlusion. Prior to designing the present invention, the only solution was to carry out the work on an articulator that did not preserve the patient's real motions. In this clinical situation, the invention aims at transposing the same mandibular kinematics, comfortable for the patient, to a new position of the mandibular arch. The new space created will be filled with new prosthetic devices the shape and position of which will not disturb the mandibular motility.

In the case an orthodontic treatment is contemplated, the clinical approach is substantially the same as that described above. Instead of filling the space with prostheses, the teeth will be moved and brought into meshing. In this case, the occlusion will also be carried out in accordance with the patient's true motions.

Also in orthodontics it will be possible to export the position with the kinematics attached thereto after closing the vertical dimension of occlusion following correction of a prematurity hindering the closing path. This corrected intermaxillary relationship with the associated motions will be useful for planning orthodontic treatment and preparing contrivances to perform the treatment in a more predictable way.

REFERENCES

WO 2013/030511
WO 2016/062962
[1] Jean-Francois Lasserre, "Comprendre l'augmentation de DVO dans les approches minimales invasives des traitements de l'usure et des anomalies de l'émail", Quintessence International

The invention claimed is:

1. A method for animating models of a patient's mandibular and maxillary arches in a corrected intermaxillary relationship, said method being computer-implemented and comprising:
   receiving three-dimensional digital models of the patient's mandibular and maxillary arches,
   receiving a record of the patient's mandibular kinematics, said record comprising a plurality of relative positions of the patient's mandible relative to to the maxilla,
   selecting, from said positions, a reference position (X) of the mandible relative to the patient's maxilla,
   determining a target position (Y) of the mandible relative to the maxilla, said target position defining the patient's corrected intermaxillary relationship without changing the patient's mandibular kinematics,
   determining a rigid transformation between the reference position (X) and the target position (Y), and
   applying said rigid transformation to (i) the record of the patient's mandibular kinematics to animate the three-dimensional digital models of the mandibular and maxillary arches, or (ii) the three-dimensional digital model of the mandible, the record of the mandibular kinematics provided being applied to the three-dimensional digital models of the mandible and maxilla to animate said models.

2. The method according to claim 1, wherein the record of the patient's mandibular kinematics describes the trajectory of markers integral with the mandible, and the rigid transformation is a transformation for switching from the position of the markers in the reference position to the position of the markers in the target position.

3. The method according to claim 1, wherein the target position is chosen by a user.

4. The method according to claim 1, comprising automatically preselecting a set of relative positions of the mandible relative to the maxilla, said set of positions being chosen such that each position of said set defines a vertical dimension of occlusion within a determined range.

5. The method according to claim 4, wherein the preselection is made from previously provided clinical criteria.

6. The method according to claim 1, wherein the target position is chosen so as to increase a vertical dimension of occlusion by a value less than a threshold chosen so as not to cause movement of the axis of rotation of the mandibular condyles relative to the patient's temporal fossa.

7. The method according to claim 1, wherein the target position is chosen so as to increase a vertical dimension of occlusion defined at an incisor crown end by less than 20 mm relative to a vertical dimension of occlusion defined by the patient's reference occlusal position.

8. The method according to claim 1, wherein the target position is chosen so as to decrease a vertical dimension of occlusion.

9. The method according to claim 1, comprising determining an axis of rotation of the mandible and creating virtual positions of the mandible in the path of the rotation towards increasing or decreasing the vertical dimension of occlusion, the target position being chosen from said virtual positions.

10. The method according to claim 1, wherein in said animating the models of the mandibular and maxillary arches, a reference occlusal position of the mandible relative to the maxilla in the corrected intermaxillary relationship becomes the target position.

11. The method according to claim 1, comprising, from the record of the mandibular kinematics, tracing a mastication pattern and comparing said pattern with a typical functional pattern.

12. The method according to claim 1, wherein the reference position is the patient's reference occlusal position prior to correcting the intermaxillary relationship.

13. A method for animating models of a patient's mandibular and maxillary arches in a corrected intermaxillary relationship, said method being computer-implemented and comprising:
   receiving three-dimensional digital models of the patient's mandibular and maxillary arches,
   receiving a record of the patient's mandibular kinematics, said record comprising a plurality of relative positions of the patient's mandible relative to to the maxilla,
   automatically preselecting a set of relative positions of the mandible relative to the maxilla, said set of positions being chosen such that each position of said set defines a vertical dimension of occlusion within a determined range,
   selecting, from said positions, a reference position (X) of the mandible relative to the patient's maxilla,
   determining a target position (Y) of the mandible relative to the maxilla, said target position defining the patient's corrected intermaxillary relationship,
   determining a rigid transformation between the reference position (X) and the target position (Y), and
   applying said rigid transformation to (i) the record of the patient's mandibular kinematics to animate the three-dimensional digital models of the mandibular and maxillary arches, or (ii) the three-dimensional digital model of the mandible, the record of the mandibular kinematics provided being applied to the three-dimensional digital models of the mandible and maxilla to animate said models.

14. A method for animating models of a patient's mandibular and maxillary arches in a corrected intermaxillary relationship, said method being computer-implemented and comprising:
   receiving three-dimensional digital models of the patient's mandibular and maxillary arches, receiving a record of the patient's mandibular kinematics, said record comprising a plurality of relative positions of the patient's mandible relative to to the maxilla, selecting, from said positions, a reference position (X) of the mandible relative to the patient's maxilla, determining a target position (Y) of the mandible relative to the maxilla, said target position defining the patient's corrected intermaxillary relationship, wherein the target position is chosen so as to increase a vertical dimension of occlusion by a value less than a threshold chosen so as not to cause movement of the axis of rotation of the mandibular condyles relative to the patient's temporal fossa, determining a rigid transformation between the reference position (X) and the target position (Y), and applying said rigid transformation to (i) the record of the patient's mandibular kinematics to animate the three-dimensional digital models of the mandibular and maxillary arches, or (ii) the three-dimensional digital model of the mandible, the record of the mandibular kinematics provided being applied to the three-dimensional digital models of the mandible and maxilla to animate said models.

15. A method for animating models of a patient's mandibular and maxillary arches in a corrected intermaxillary relationship, said method being computer-implemented and comprising:

receiving three-dimensional digital models of the patient's mandibular and maxillary arches, receiving a record of the patient's mandibular kinematics, said record comprising a plurality of relative positions of the patient's mandible relative to to the maxilla, selecting, from said positions, a reference position (X) of the mandible relative to the patient's maxilla, determining a target position (Y) of the mandible relative to the maxilla, said target position defining the patient's corrected intermaxillary relationship, wherein the target position is chosen so as to increase a vertical dimension of occlusion defined at an incisor crown end by less than 20 mm relative to a vertical dimension of occlusion defined by the patient's reference occlusal position, determining a rigid transformation between the reference position (X) and the target position (Y), and applying said rigid transformation to (i) the record of the patient's mandibular kinematics to animate the three-dimensional digital models of the mandibular and maxillary arches, or (ii) the three-dimensional digital model of the mandible, the record of the mandibular kinematics provided being applied to the three-dimensional digital models of the mandible and maxilla to animate said models.

* * * * *